United States Patent
McLaughlin

(10) Patent No.: US 11,633,173 B2
(45) Date of Patent: *Apr. 25, 2023

(54) WIRELESSLY PROGRAMMABLE TRANSDUCER-BASED REMOTE CONTROL WITH INERTIAL SENSOR

(71) Applicant: Shenzhen Mindray Bio-Medical Electronics Co., Ltd., Shenzhen (CN)

(72) Inventor: Glen W. McLaughlin, San Carlos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/941,328

(22) Filed: Sep. 9, 2022

(65) Prior Publication Data

US 2023/0000465 A1    Jan. 5, 2023

Related U.S. Application Data

(63) Continuation of application No. 16/040,264, filed on Jul. 19, 2018, now Pat. No. 11,484,290.

(51) Int. Cl.
*A61B 8/00* (2006.01)
*G06F 3/01* (2006.01)
*G06F 3/041* (2006.01)
*G16H 30/20* (2018.01)
*G06T 7/00* (2017.01)

(52) U.S. Cl.
CPC ............ *A61B 8/4472* (2013.01); *A61B 8/469* (2013.01); *G06F 3/017* (2013.01); *G06F 3/041* (2013.01); *G06T 7/0012* (2013.01); *G16H 30/20* (2018.01); *A61B 8/565* (2013.01); *G06T 2207/10132* (2013.01); *G06T 2207/30068* (2013.01)

(58) Field of Classification Search
None
See application file for complete search history.

(56) References Cited

U.S. PATENT DOCUMENTS

| | | |
|---|---|---|
| 2003/0013959 A1 | 1/2003 | Grunwald |
| 2010/0160784 A1 | 6/2010 | Poland |
| 2011/0320153 A1 | 12/2011 | Lightcap |
| 2012/0022379 A1 | 1/2012 | Gubbini |
| 2014/0276055 A1 | 9/2014 | Barthe |
| 2015/0327841 A1 | 11/2015 | Banjanin |

(Continued)

*Primary Examiner* — Katherine L Fernandez
(74) *Attorney, Agent, or Firm* — Kory D. Christensen

(57) ABSTRACT

Systems and methods are disclosed for remotely controlling a main processing console of an ultrasound system. In various embodiments, an ultrasound remote controller can be used to remotely control a main processing console of an ultrasound system. The ultrasound remote controller can include a user interface controller configured to provide one or more ultrasound control functions to a user remote from the main processing console. The control functions can be used to remotely control operation of the main console. Further, the user interface controller can be configured to receive input for the one or more ultrasound control functions from the user. The ultrasound remote controller can include a communication interface configured to transmit operational instructions to the main processing console for remotely controlling the operation of the main processing console through the ultrasound remote controller based on the user input for the one or more ultrasound control functions.

20 Claims, 6 Drawing Sheets

(56) References Cited

U.S. PATENT DOCUMENTS

| | | |
|---|---|---|
| 2017/0273665 A1 | 9/2017 | Kapoor |
| 2018/0228462 A1 | 8/2018 | Maghsoudnia |
| 2018/0271484 A1 | 9/2018 | Whisler |
| 2019/0380676 A1 | 12/2019 | Swan |

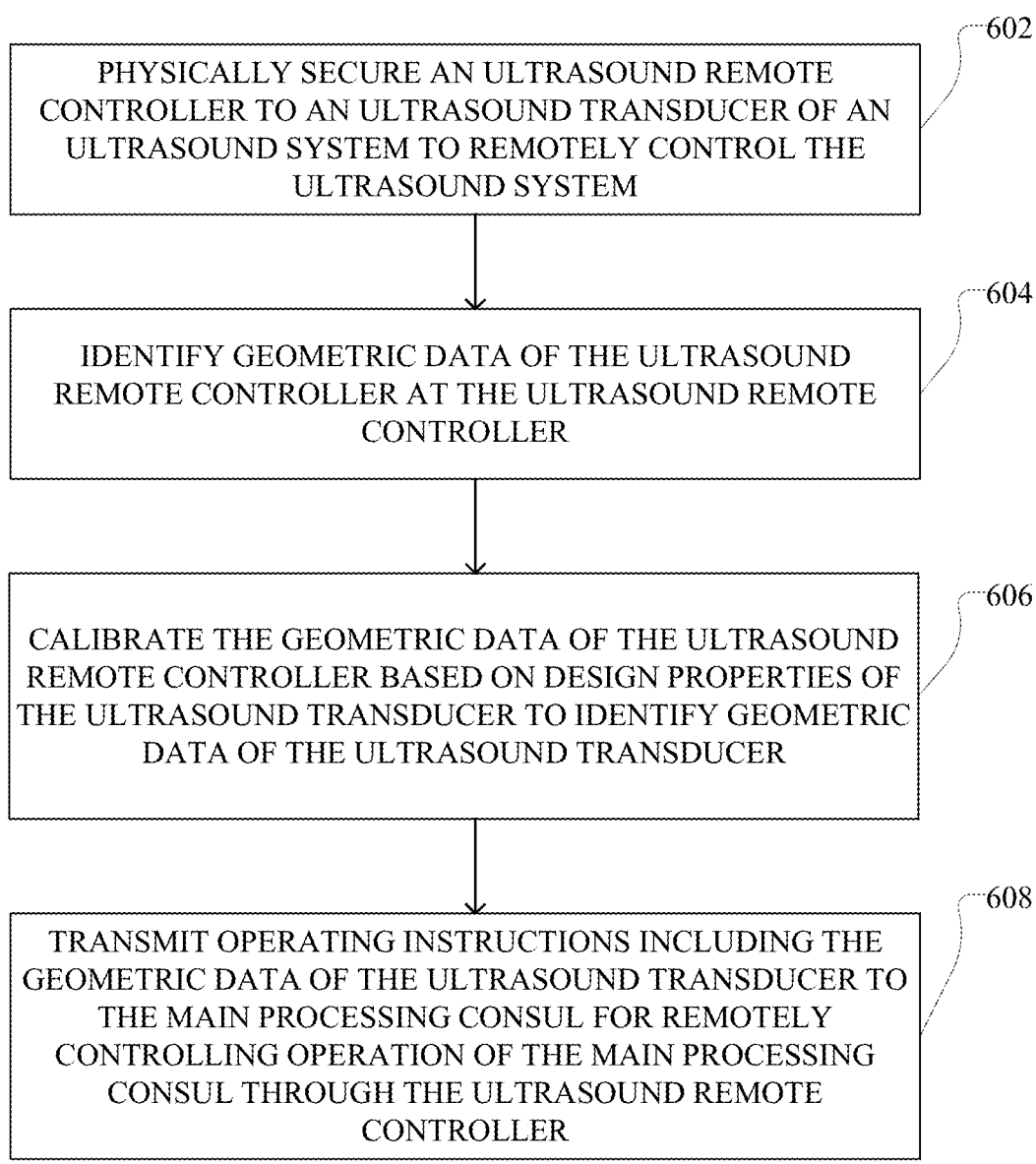

WIRELESSLY PROGRAMMABLE TRANSDUCER-BASED REMOTE CONTROL WITH INERTIAL SENSOR

CROSS-REFERENCE TO RELATED APPLICATIONS

This application is a continuation of U.S. patent application Ser. No. 16/040,264, filed Jul. 19, 2018, for WIRELESSLY PROGRAMMABLE TRANSDUCER-BASED REMOTE CONTROL WITH INERTIAL SENSOR, which is incorporated herein by reference.

TECHNICAL FIELD

This disclosure relates to remotely controlling an ultrasound system. Specifically, this disclosure relates to remotely controlling a main processing console of an ultrasound system using an ultrasound remote controller based on input received at the ultrasound remote controller from a user of the ultrasound system.

BACKGROUND OF THE INVENTION

Ultrasound imaging is a widely used for examining a wide range of materials and objects across a wide array of different applications. Ultrasound imaging provides a fast and easy tool for analyzing materials and objects in a non-invasive manner. As a result, ultrasound imaging is especially common in the practice of medicine as an ailment diagnosis, treatment, and prevention tool. Specifically, because of its relatively non-invasive nature, low cost and fast response time ultrasound imaging is widely used throughout the medical industry to diagnose and prevent ailments. Further, as ultrasound imaging is based on non-ionizing radiation it does not carry the same risks as other diagnosis imaging tools, such as X-ray imaging or other types of imaging systems that use ionizing radiation.

Ultrasound imaging is accomplished by generating and directing ultrasonic sound waves into a material of interest, first in a transmit phase and subsequently in a receive phase. During the transmit phase, an ultrasonic signal is transmitted into a material of interest by applying continuous or pulsed electronic signals. During the receive phase, reflections generated by boundaries between dissimilar materials are received by receiving devices, such as transducers, and converted to electrical signals. Signals can then be processed to determine the locations of the echo sources. The resulting data can be used to display images of inside a material of interest, e.g. by displaying images using a display device, such as a monitor.

Ultrasound imaging can offer a wealth of clinical information. Specifically, ultrasound imaging can be used in abdominal ultrasound (to visualize abdominal tissues and organs), bone sonometry (to assess bone fragility), breast ultrasound (to visualize breast tissue), Doppler fetal heart rate monitors (to listen to a fetal heart beat), Doppler ultrasound (to visualize blood flow through a blood vessel, organs, or other structures), echocardiogram (to view a heart), fetal ultrasound (to view a fetus in pregnancy), ultrasound-guided biopsies (to collect a sample of tissue), ophthalmic ultrasound (to visualize ocular structures) and ultrasound-guided needle placement (in blood vessels or other tissues of interest). Ultrasound imaging has also been used in describing various disease states, such as diseases of the liver, breast, prostate, thyroid or other organs through single measurements of stiffness or shear wave velocity.

Typically ultrasound systems include a main processing console and an ultrasound transducer. The ultrasound transducer is positioned away from the main console and actively controlled by an operator in gathering ultrasound image data. In turn, an operator has to be able to control a number of functions away from the main system console. In the past this was accomplished via a foot pedal or having an assistant present to operate the main system console separately from the operator. However, the use of foot pedals is awkward and can lead to difficulties in controlling or inabilities to control the main system console. Further, the use of separate assistants can present additional challenges in controlling the main system console, e.g. the need for effective communication skills and an increased potential from errors created by unskilled assistants.

Additionally, in many ultrasound imaging scenarios, an operator needs two hands to operation an ultrasound transducer. This requires the operator to dedicate their full attention to operating the ultrasound transducer. In turn, this makes foot pedals of the use of assistants to control a main system console nearly impossible, as the focus of the operator is to both of their hands and manipulating the ultrasound transducer. In particular, this is important for interventional procedures where operators have to biopsy or aspirate an area of tissue.

There therefore exist needs for systems and methods that allow an operator to remotely control a main system console of an ultrasound system. Specifically, there exists a need for systems and methods for allowing an operator to remotely control a main system console of an ultrasound system while the operator manipulates an ultrasound transducer of the ultrasound system. More specifically, there exists a need for systems and methods that are integrated along with an ultrasound transducer to allow an operator to control a main processing console of an ultrasound system while the operator manipulates the ultrasound transducer. Further, there exists a need for systems and methods for allowing an operator to remotely control a main processing console of existing ultrasound systems without having to purchase an entire new ultrasound system.

SUMMARY

According to various embodiments, an ultrasound remote controller is configured to remotely control a main processing console of an ultrasound system. The ultrasound remote controller can include a user interface controller. The user interface controller can be configured to provide one or more ultrasound control functions to a user remote from the main processing console of the ultrasound system including an ultrasound transducer. The one or more ultrasound control functions can be used to remotely control operation of the main processing console. Further, the user interface controller can be configured to receive input for the one or more ultrasound control functions from the user for remotely controlling the operation of the main processing console. The ultrasound remote controller can include a communication interface. The communication interface can be configured to transmit operational instructions to the main processing console for remotely controlling the operation of the main processing console through the ultrasound remote controller based on the input for the one or more ultrasound control functions received by the user interface controller.

In various embodiments, one or more ultrasound control functions are provided to a user through an ultrasound remote controller remote from a main processing console of an ultrasound system including an ultrasound transducer.

The one or more ultrasound control functions can be used to remotely control operation of the main processing console. Further, input from the user is received at the ultrasound remote controller for the one or more ultrasound control functions to remotely control the operation of the main processing console. Additionally, operational instructions can be transmitted to the main processing console for remotely controlling the operation of the ultrasound system through the ultrasound remote controller. The operational instructions can be generated based on or otherwise include the input for the one or more ultrasound control functions received at the ultrasound remote controller.

In certain embodiments, an ultrasound remote controller is physically secured to an ultrasound transducer of an ultrasound system including a main processing console. Geometric data of the ultrasound remote controller can be identified. The geometric data of the ultrasound remote controller can include one or a combination of a motion, a position, and an orientation of the ultrasound remote controller. Further, the geometric data of the ultrasound remote controller can be calibrated based on design properties of the ultrasound transducer to identify geometric data of the ultrasound transducer. The geometric data of the ultrasound transducer can be transmitted as part of operational instructions to the main processing console for remotely controlling operation of the main processing console through the ultrasound remote controller.

BRIEF DESCRIPTION OF THE DRAWINGS

FIG. 6 is a flowchart of another example method of remotely controlling an ultrasound system through an ultrasound remote controller.

DETAILED DESCRIPTION

Figure 1:
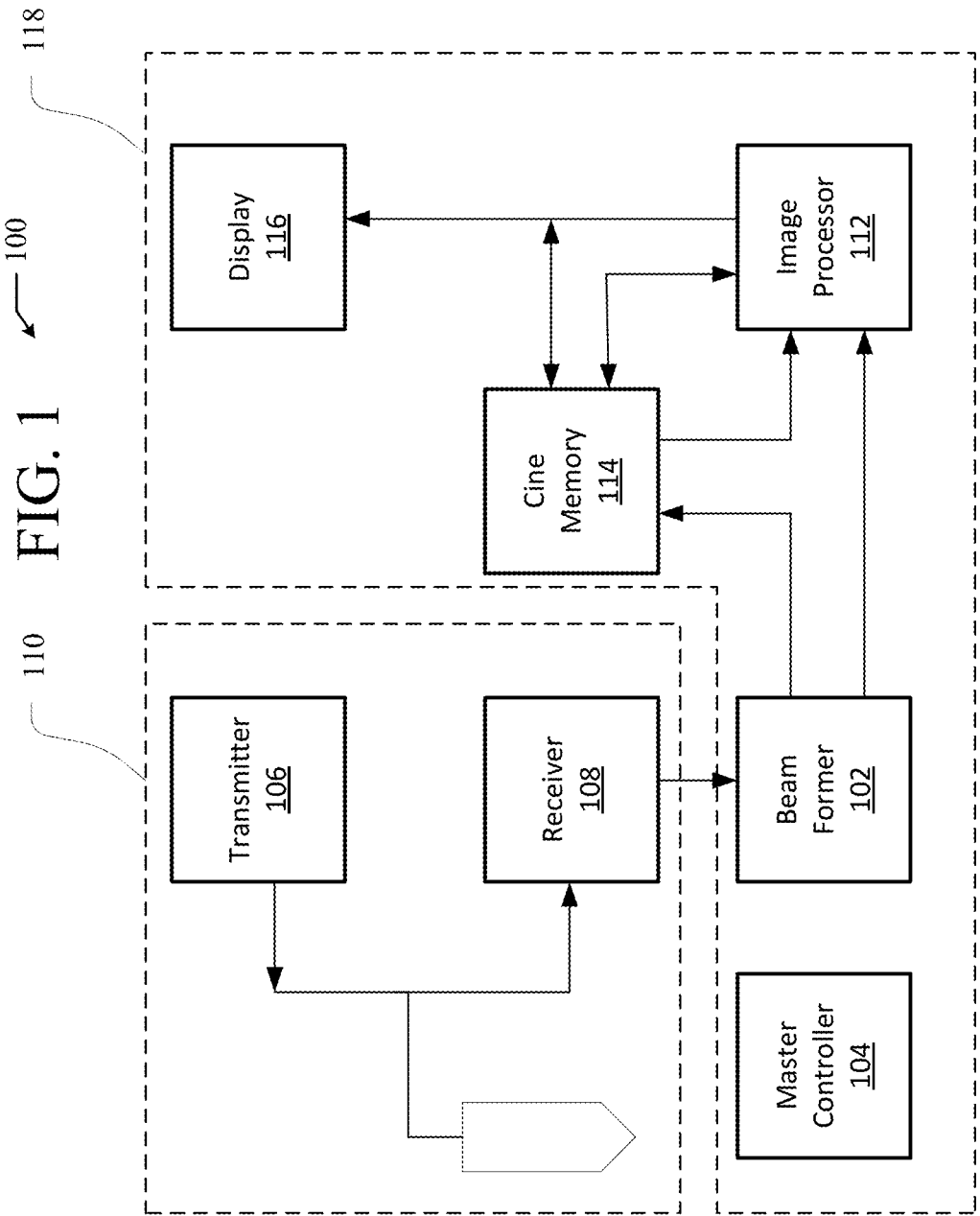
FIG. 1 illustrates an example of an ultrasound system.

According to various embodiments, an ultrasound remote controller is configured to remotely control a main processing console of an ultrasound system. The ultrasound remote controller can include a user interface controller. The user interface controller can be configured to provide one or more ultrasound control functions to a user remote from the main processing console of the ultrasound system including an ultrasound transducer. The one or more ultrasound control functions can be used to remotely control operation of the main processing console. Further, the user interface controller can be configured to receive input for the one or more ultrasound control functions from the user for remotely controlling the operation of the main processing console. The ultrasound remote controller can include a communication interface. The communication interface can be configured to transmit operational instructions to the main processing console for remotely controlling the operation of the main processing console through the ultrasound remote controller based on the input for the one or more ultrasound control functions received by the user interface controller.

In various embodiments, one or more ultrasound control functions are provided to a user through an ultrasound remote controller remote from a main processing console of an ultrasound system including an ultrasound transducer. The one or more ultrasound control functions can be used to remotely control operation of the main processing console. Further, input from the user is received at the ultrasound remote controller for the one or more ultrasound control functions to remotely control the operation of the main processing console. Additionally, operational instructions can be transmitted to the main processing console for remotely controlling the operation of the ultrasound system through the ultrasound remote controller. The operational instructions can be generated based on, or otherwise include, the input for the one or more ultrasound control functions received at the ultrasound remote controller.

In certain embodiments, an ultrasound remote controller is physically secured to an ultrasound transducer of an ultrasound system including a main processing console. Geometric data of the ultrasound remote controller can be identified. The geometric data of the ultrasound remote controller can include one or a combination of a motion, a position, and an orientation of the ultrasound remote controller. Further, the geometric data of the ultrasound remote controller can be calibrated based on design properties of the ultrasound transducer to identify geometric data of the ultrasound transducer. The geometric data of the ultrasound transducer can be transmitted as part of operational instructions to the main processing console for remotely controlling operation of the main processing console through the ultrasound remote controller.

Some of the infrastructure that can be used with embodiments disclosed herein is already available, such as general-purpose computers, antennas, computer programming tools and techniques, digital storage media, and communications networks. A computing device may include a processor such as a microprocessor, microcontroller, logic circuitry, or the like. The processor may include a special purpose processing device such as an ASIC, PAL, PLA, PLD, FPGA, or other customized or programmable device. The computing device may also include a computer-readable storage device such as non-volatile memory, static RAM, dynamic RAM, ROM, CD-ROM, disk, tape, magnetic, optical, flash memory, or other computer-readable storage medium.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

FIG. 1 illustrates an example of an ultrasound system 100. The ultrasound system 100 shown in FIG. 1 is merely an example system and in various embodiments, the ultrasound system 100 can have less components or additional components. Specifically, the ultrasound system 100 includes is an ultrasound system where the receive array focusing unit is referred to as a beam former 102, and image formation can be performed on a scanline-by-scanline basis. System control can be centered in the master controller 104, which accepts operator inputs through an operator interface and in turn controls the various subsystems. For each scan line, the transmitter 106 generates a radio-frequency (RF) excitation voltage pulse waveform and applies it with appropriate timing across the transmit aperture (defined by a sub-array of active elements) to generate a focused acoustic beam along the scan line. RF echoes received by the receive aperture 108 of the transducer 110 are amplified and filtered by the receiver 108, and then fed into the beam former 102, whose function is to perform dynamic receive focusing; i.e., to re-align the RF signals that originate from the same locations along various scan lines.

The image processor 112 can perform processing specific to active imaging mode(s) including 2D scan conversion that transforms the image data from an acoustic line grid to an X-Y pixel image for display. For Spectral Doppler mode, the image processor 112 can perform wall filtering followed by spectral analysis of Doppler-shifted signal samples using typically a sliding FFT-window. The image processor 112 can also generate the stereo audio signal output corresponding to forward and reverse flow signals. In cooperation with the master controller 104, the image processor 112 also can format images from two or more active imaging modes, including display annotation, graphics overlays and replay of cine loops and recorded timeline data.

The cine buffer 114 provides resident digital image storage for single image or multiple image loop review, and acts as a buffer for transfer of images to digital archival devices. On most systems, the video images at the end of the data processing path can be stored to the cine memory. In state-of-the-art systems, amplitude-detected, beam formed data may also be stored in cine memory 114. For spectral Doppler, wall-filtered, baseband Doppler I/Q data for a user-selected range gate can be stored in cine memory 114. Subsequently, the display 11 can display ultrasound images created by the image processor 112 and/or images using data stored in the cine memory 114.

The beam former 102, the master controller 104, the image processor, the cine memory 114, and the display can be included as part of a main processing console 118 of the ultrasound system 100. In various embodiments, the main processing console 118 can include more or fewer components or subsystems. The ultrasound transducer 110 can be incorporated in an apparatus that is separate from the man processing console 118, in a separate apparatus that is wired or wirelessly connected to the main processing console 118. This allows for easier manipulation of the ultrasound transducer 110 when performing specific ultrasound procedures on a patient.

Figure 2:
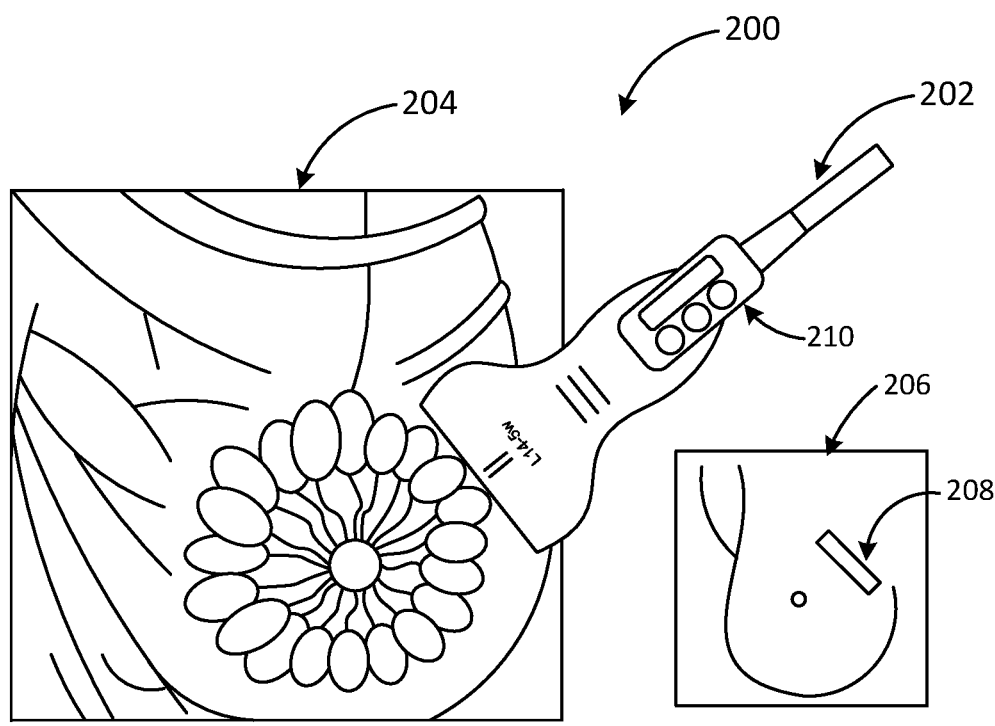
FIG. 2 illustrates an example system for remotely controlling a main processing console of an ultrasound system.

FIG. 2 illustrates an example system 200 for remotely controlling a main processing console of an ultrasound system. The main processing console can be an applicable main processing console for processing ultrasound image data in an ultrasound system, such as the main processing console 118 show in the example system 100 in FIG. 1. The system 200 is shown with respect to scanning of a breast. Specifically, the system 200 includes a linear transducer/ultrasound transducer 202 with respect to a breast for purposes of scanning the breast is shown in FIG. 2. A sketch of the anatomy of a breast is shown in 204. The linear transducer 202 is in contact with the breast in the upper left region of the right breast. This position is self-annotated in the body marker image of the right breast, 206, with the linear transducer position/orientation indicator, 208.

The example system 200 shown in FIG. 2 includes an ultrasound remote controller 210. The ultrasound remote controller 210 functions to provide an operator of an ultrasound system, e.g. the ultrasound system 100 in FIG. 1, with functionalities for remotely controlling a main processing console of the ultrasound system. Specifically, the ultrasound remote controller 210 can be used by an operator to remotely control a main processing console of an ultrasound system when the user is away from the main processing console, e.g. manipulating the ultrasonic transducer 202. In turn, this can allow the operator to focus more completely on manipulating the ultrasonic transducer 202 in gathering ultrasonic image data, while still controlling processing of the ultrasonic image data. Accordingly, the need for an operator to rely on complex foot pedal controls or separate assistants can be reduced or otherwise eliminated. This can increase the ease by which an operator can conduct an ultrasound procedure and potentially reduce a number of people that are needed to perform the procedure.

In providing an operator of an ultrasound system with functionalities for remotely controlling a main processing console of an ultrasound system, the ultrasound remote controller 210 can provide ultrasound control functions to the operator. More specifically, the ultrasound remote controller 210 can provide an operator with control functions for controlling a main processing console of an ultrasound system through a user interface controller, e.g. a user interface. A user interface controller can include either or both display and applicable production mechanisms for producing available functionalities for remotely controlling a main processing console of an ultrasound system. Specifically, a user interface controller can include mechanisms for producing available functionalities for remotely controlling a main processing console in a manner that is perceivable by an operator. For example, a user interface can include a display for presenting visual annotations of available ultrasound control functions to an operator. In another example, a user interface can include a haptic device for producing haptic feedback for corresponding available ultrasound control functions.

A display included in a user interface controller of the ultrasound remote controller 210 can include an organic light emitting diode (herein "OLED") based display. Further, a display included in a user interface controller of the ultrasound remote controller 210 can include a light emitting diode (herein "LED") based display. Additionally, a display included in a user interface controller of the ultrasound remote controller 210 can be a liquid-crystal display (herein "LCD") including liquid crystals and a backlight or reflector to visually present available functionalities for remotely controlling a main processing console.

Ultrasound control functions include applicable functionalities for controlling a main processing console of an ultrasound system, e.g. remote from the main processing console of the ultrasound system. Specifically ultrasound control functions can include applicable functions that a user can provide input for to control a main processing console in gathering, processing, and reproducing ultrasound images as part of an ultrasound procedure.

An ultrasound control function can include a freeze control function. For example, an ultrasound control function can include a control for freezing a display at a specific ultrasound image. Additionally, an ultrasound control function can include a depth control function for changing a depth of field or focus for gathering ultrasound image data. Further, an ultrasound control function can include a gain control for adjusting amplification of received/reflected signals for ultrasound images. An ultrasound control function can also include a storage control for controlling how data of ultrasound image data is stored and subsequently processed to reproduce ultrasound images. Further, an ultrasound control function can include an auto-optimization control for enabling automatic optimization of either or both a gain and an overall contrast in an ultrasound image. Additionally, an ultrasound control function can include a set reference control for specifying and selecting a reference frame for ultrasound imaging. An ultrasound control function can also include a start clip control to control creation of an ultrasound clip. Further, an ultrasound control function can include a change mode control for controlling an image mode used to gather and process ultrasound images in an ultrasound procedure. Additionally, an ultrasound control function can include a move region of interest control that is used to adjust a region of interest in a medium scanned during an ultrasound procedure. An ultrasound control function can also include a biopsy guide control for adjusting presentation of a biopsy guide in an ultrasound procedure. Further, an ultrasound control function can include a body marker select control for selecting a body marker image used in an ultrasound procedure.

The user interface controller of the ultrasound remote controller 210 can dynamically select ultrasound control functions to provide to an operator and subsequently provide the dynamically selected ultrasound control functions to the operator. For example, the user interface controller can dynamically determine to begin providing an auto-optimization control to an operator during a procedure, and subsequently begin providing the auto-optimization control to the operator during the procedure. In another example, the user interface controller can dynamically determine to stop providing a start clip control to an operator during a procedure, and subsequently stop providing the start clip control to the operator during the procedure.

In various embodiments, the user interface controller of the ultrasound remote controller 210 can dynamically select ultrasound control functions to provide to an operator based on a context of an ultrasound procedure. More specifically, the user interface controller can dynamically select ultrasound control functions to provide to an operator based on a context of one or a combination of a past procedure performed by the operator, a procedure being performed by the operator, or a future procedure that will be performed by the operator. A context of an ultrasound procedure can include circumstances or characteristics of an ultrasound procedure. For example, a context of an ultrasound procedure can include whether the ultrasound procedure is a biopsy procedure. Further in the example, based on the context that the ultrasound procedure if a biopsy procedure, the user interface controller can provide a biopsy guide control to an operator during the ultrasound procedure.

Associations of specific ultrasound control functions and specific ultrasound procedure contexts can be used by the user interface controller of the ultrasound remote controller 210 to provide ultrasound control functions based on specific contexts. For example, if a start clip control functions is associated with an ultrasound fetal imaging procedure, then a user interface controller can provide the start clip control function when a fetal imaging procedure is performed according to the association of the function with fetal imaging. Associations of specific ultrasound control functions and specific ultrasound procedure contexts can be pre-programmed into the ultrasound remote controller 210, e.g. before operation of the ultrasound remote controller 210. Further, associations of specific ultrasound control functions and specific ultrasound procedure contexts can be transmitted to the ultrasound remote controller 210, e.g. wirelessly transmitted to the controller 210 during operation of the ultrasound remote controller 210.

The ultrasound remote controller 210 can receive input for controlling a main processing console of an ultrasound controller from an operator. Specifically, the ultrasound remote controller 210 can receive input for one or more ultrasound control functions for controlling a main processing console of an ultrasound system through a user interface controller, e.g. a user interface. Input for one or more ultrasound control functions for controlling a main processing console of an ultrasound system can include values of one or more variables of corresponding ultrasound control functions. For example, input for one or more ultrasound control functions can include a gain value for adjusting amplification of received/reflected signals for ultrasound images, as part of a gain control.

A user interface controller of the ultrasound remote controller 210 can include applicable controls for generating and receiving input by an operator for remotely controlling a main processing console of an ultrasound system. For example, the user interface controller can include a touch-based display through which an operator can provide touch-based input for remotely controlling a main processing console of an ultrasound system. In another example, the user interface controller can include a camera or other motion detection sensor through which an operator can provide gesture-based input for remotely controlling a main processing console of an ultrasound system.

Further, a user interface controller of the ultrasound remote controller 210 can include one or more physical buttons and sliders capable of being physically manipulated by an operator to generate input for remotely controlling a main processing console of an ultrasound system. Physical buttons and sliders can be associated with or otherwise used to provide input for specific ultrasound control functions. For example, a button included as part of the user interface controller can be used to control a body marker control function. Specific ultrasound control functions associated with specific physical buttons and sliders can change dynamically, e.g. based on what ultrasound control functions are provided to an operator. For example, a button in a user interface controller of the ultrasound remote controller 210 can be used as a biopsy guide controller during a biopsy ultrasound procedure. Further in the example, the same button can be used as a set reference control during a different ultrasound procedure.

A user interface controller of the ultrasound remote controller 210 can receive input for remotely controlling a main processing console based on haptic feedback. Specifically, a user interface controller of the ultrasound remote controller 210 can receive input for one or more ultrasound control functions in response to presenting the control functions to an operator through haptic feedback. For example, the ultrasound remote controller 210 can shake to signify to an operator that a new ultrasound control function is available to the operator. Subsequently, the user interface controller can receive input for the new ultrasound control feedback in response to the haptic feedback provided to the operator.

Further, a user interface controller of the ultrasound remote controller 210 can receive input for remotely controlling a main processing console based on visual annotations. Specifically, a user interface controller of the ultrasound remote controller 210 can receive input based on an operator's interaction with visual annotations of one or more ultrasound control functions. For example, an operator can interact with a visual annotation of a set reference control to indicate a frame as a reference frame. Subsequently, the user interface controller can receive input indicating the frame is the reference frame based on the operator interacting with the visual annotation of the set reference control.

A user interface controller of the ultrasound remote controller 210 can generate operational instructions for remotely controlling a main processing console of an ultrasound system. Operational instructions can include instructions detailing how a main processing console of an ultrasound system should operate in gathering ultrasound image data, processing ultrasound image data, and displaying ultrasound image data. For example, operational instructions can instruct to adjust a depth of field focus for gathering ultrasound image data. The user interface controller can generate operational instructions based on input for ultrasound control functions received by the user interface controller. Specifically, the user interface controller can generate operational instructions specifying to operate the main processing console according to specific commands represented in input received from an operator. Further, the user interface controller can generate operational instructions by actually including input received for ultrasound control functions in the operational instructions.

The ultrasound remote controller 210 can include a communication interface configured to provide the operational instructions to a main processing console of an ultrasound system for controlling the ultrasound system. Specifically, the communication interface of the ultrasound remote controller 210 can provide operational instructions to a main processing console of an ultrasound system in order to remotely control the ultrasound system. For example, the communication interface of the ultrasound remote controller 210 can provide operational instructions to a main processing console of an ultrasound system for purposes of remotely controlling operation of the main processing console. In another example, the communication interface of the ultrasound remote controller 210 can provide operational instructions to a main processing console of an ultrasound system for purposes of remotely controlling operation of an ultrasound transducer of the ultrasound system, e.g. through the main processing console.

A communication interface of the ultrasound remote controller 210 can communicate with or transmit operational instructions to a main processing console of an ultrasound system according to an applicable communication protocol. Specifically, the communication interface of the ultrasound remote controller 210 can transmit operational instructions to the main processing console through a wired connection. For example, a wired connection can be directly formed between the communication interface and the main processing console and be used to transmit operational instructions from the communication interface to the main processing console. Alternatively, a wired connection can be formed between the communication interface and the main processing console through an ultrasound transducer. Subsequently, the wired connection can be used to transmit operational instructions from the communication interface to the main processing console through the ultrasound transducer.

Further, a communication interface of the ultrasound remote controller 210 can communicate, at least in part, with a main processing console of an ultrasound system through a wireless connection. Specifically, the communication interface can be configured to communicate through an applicable wireless communication protocol, e.g. a Bluetooth, ZigBee, or 802.11 wireless protocol. For example, the communication interface can be configured to transmit operational instructions to the main processing console over a Wi-Fi connection.

In communicating over a wireless connection, a communication interface of the ultrasound remote controller 210 can receive instructions for programming the ultrasound remote controller 210 over the wireless connection. Specifically, the communication interface can receive instructions for programming a user interface controller over a wireless connection, e.g. from the main processing console of the ultrasound system. For example, the communication interface can receive associations of ultrasound control functions and contexts of ultrasound procedures over a wireless connection which can subsequently be used to program a user interface controller to present the ultrasound control functions according to the contexts of the ultrasound procedures.

By communicating over a wireless communication interface, the ultrasound remote controller 210 can be operated remote from an ultrasound transducer. Specifically, an operator can interact with the ultrasound remote controller 210 while the controller 210 is remote from an ultrasound transducer as the operator manipulates the ultrasound transducer during an ultrasound procedure. This eliminates the need for an operator to use foot pedals or a separate assistant to control a main processing console during an ultrasound procedure. In turn, this allows an operator to focus more on manipulating an ultrasound transducer during an ultrasound procedure.

Alternatively, the ultrasound remote controller 210, as shown in FIG. 2, can be physically coupled or affixed to the ultrasound transducer 202. Specifically, in the system 200 shown in FIG. 2, the ultrasound remote controller 210 is attached to the ultrasound transducer 202 at the junction between the transducer handle and the cable interconnect so that it is out of the way from the main grip areas of the transducer. By being affixed to the ultrasound transducer 202, an operator can simultaneously manipulate the ultrasound transducer 202 and operate the ultrasound remote controller 210 to remotely control a main processing console of an ultrasound system. Specifically, an operator can simultaneously operate both the ultrasound transducer 202 and the ultrasound remote controller 210 using a single hand or both hands. This eliminates the need for an operator to use foot pedals or a separate assistant to control a main processing console during an ultrasound procedure. In turn, this allows an operator to focus more on manipulating an ultrasound transducer during an ultrasound procedure.

The ultrasound remote controller 210 can be affixed to the ultrasound transducer 202 through a physical coupler. A physical coupler can include an applicable mechanism for physically securing the ultrasound remote controller 210 to the ultrasound transducer 202. For example, a physical coupler can include a mechanical fastener or an adhesive material. A physical coupler can be configured to removably affix the ultrasound remote controller 210 to the ultrasound transducer 202. Specifically, a physically coupler can be configured to physically affix the ultrasound remote controller 210 to the ultrasound transducer 202 and allow the ultrasound remote controller 210 to be detached from the ultrasound transducer 202 in a removable manner. This is advantageous as the ultrasound remote controller 210 can be operated with different ultrasound transducers in different ultrasound procedures. For example, an operator can use the ultrasound remote controller 210 with an ultrasound transducer in a first procedure and subsequently detach the ultrasound remote controller 210 from the transducer to use the ultrasound remote controller 210 in a different procedure using a different transducer. Further, in being removably affixed to the ultrasound transducer 202, the ultrasound remote controller 210 can easily be detached for cleaning and sterilization.

A physical coupler used to affix the ultrasound remote controller 210 to the ultrasound transducer 202 can be integrated as part of the ultrasound remote controller 210. Specifically, a physical coupler can be integrated as part of the ultrasound remote controller 210 to facilitate affixing of the ultrasound remote controller 210 to different ultrasound transducers. In turn, the ultrasound remote controller 210 can be used by a single operator in different procedures or by multiple operators in different procedures. For example, a physical coupler can include an adhesive material or magnetic material included as part of the ultrasound remote controller 210 that is used to physically affix the ultrasound remote controller 210 to different ultrasound transducers.

Further, a physical coupler used to affix the ultrasound remote controller 210 to the ultrasound transducer 202 can be configured to affix the ultrasound remote controller 210 to different types of ultrasound transducers irrespective of varying design properties of the different types of transducers. Specifically, a physical coupler can be of a shape and size to allow the ultrasound remote controller 210 to be affixed to multiple types of ultrasound transducers irrespective of their design properties. This can allow the ultrasound remote controller 210 to be used with different current ultrasound systems, thereby potentially eliminating a need for operators to purchase new ultrasound systems. This is advantageous as a standard for ultrasound transducers does not exist across manufactures and ultrasound transducers are manufactured in different shapes, sizes, and geometries.

Alternatively, a physical coupler used to affix the ultrasound remote controller 210 to the ultrasound transducer 202 can be specific to either or both a transducer type of the ultrasound transducer 202 and a manufacturer of the ultrasound transducer 202. For example, a physical coupler can be a clip unique to the ultrasound transducer 202 based on a shape, size, and geometry of the ultrasound transducer 202. Further in the example, the ultrasound remote controller 210 can be configured to attach to or otherwise couple with different clips unique to different ultrasound transducers. Accordingly, the ultrasound remote controller 210 can be compatible with multiple ultrasound transducer types made by different manufacturers.

The ultrasound remote controller 210 can include an electrical coupler for electrically coupling the ultrasound remote controller 210 to the ultrasound transducer 202. An electrical coupler can include a wireless interface to wirelessly couple the ultrasound remote controller 210 to the ultrasound transducer 202 through a wireless electrical connection. Further, an electrical coupler can include a wired interface to couple the ultrasound remote controller 210 to the ultrasound transducer 202 through a wired electrical connection.

An electrical coupler that electrically coupes the ultrasound remote controller 210 to the ultrasound transducer 202 can be integrated as part of a physical coupler used to physically affix the ultrasound remote controller 210 to the ultrasound transducer 202. Specifically, an electrical coupler can be formed through electrical contacts that integrated in a physical coupler used to affix the ultrasound remote controller 210 to the ultrasound transducer 202. More specifically, the electrical contacts can connect when the ultrasound remote controller 210 is affixed to the ultrasound transducer 202, thereby electrically connecting the ultrasound remote controller 210 to the ultrasound transducer. For example, electrical contacts can be formed through an adhesive patch that is used to affix the ultrasound remote controller 210 to the ultrasound transducer 202.

Further, an electrical coupler that electrically couples the ultrasound remote controller 210 to the ultrasound transducer 202 can be used to program the ultrasound remote controller 210. For example, electrical connections formed through an electrical coupler between the ultrasound remote controller 210 and the ultrasound transducer 202 can be used to transmit associations of specific ultrasound control functions and specific ultrasound procedure contexts to the ultrasound remote controller 210. Further, as will be discussed in greater detail later, an electrical coupler that electrically couples the ultrasound remote controller 210 to the ultrasound transducer 202 can be used to transfer power from the ultrasound transducer 202 to the ultrasound remote controller 210. For example, power can be wirelessly transferred from the ultrasound transducer 202 to the ultrasound remote controller 210 through an electrical coupler formed as part of a physical coupler for affixing the ultrasound remote controller 210 to the ultrasound transducer.

An electrical connection between the ultrasound remote controller 210 and the ultrasound transducer 202 can be used to transmit operational instructions for purposes of controlling an ultrasound system remotely. Specifically, the ultrasound remote controller 210 can provide operational instructions to a main processing console of an ultrasound system through an electrical connection formed between the ultrasound remote controller 210 and the ultrasound transducer 202. More specifically, the ultrasound remote controller 210 can transmit operational instructions to the ultrasound transducer 202 and the operational instructions can subsequently be transmitted from the ultrasound transducer 202 to a main processing console of an ultrasound system.

As will be discussed in greater detail later, the ultrasound remote controller 210 can include an inertial motion unit configured to identify geometric data of the ultrasound remote controller 210. Geometric data, as used herein, can include at least one of a motion, a position, and an orientation of an object, e.g. the ultrasound remote controller 210.

As shown in the example system 200 in FIG. 2, the ultrasound remote controller 210 is coupled to the ultrasound transducer 202. Therefore geometric data of the ultrasound remote controller 210 can correspond to geometric data for the ultrasound transducer 202. Accordingly, as shown in FIG. 2, using the geometric data of the ultrasound remote controller 210 and corresponding geometric data for the ultrasound transducer 202, the indicator 208 of the ultrasound transducer 202 in relation to the breast can be displayed in the body marker image 206.

Figure 3:
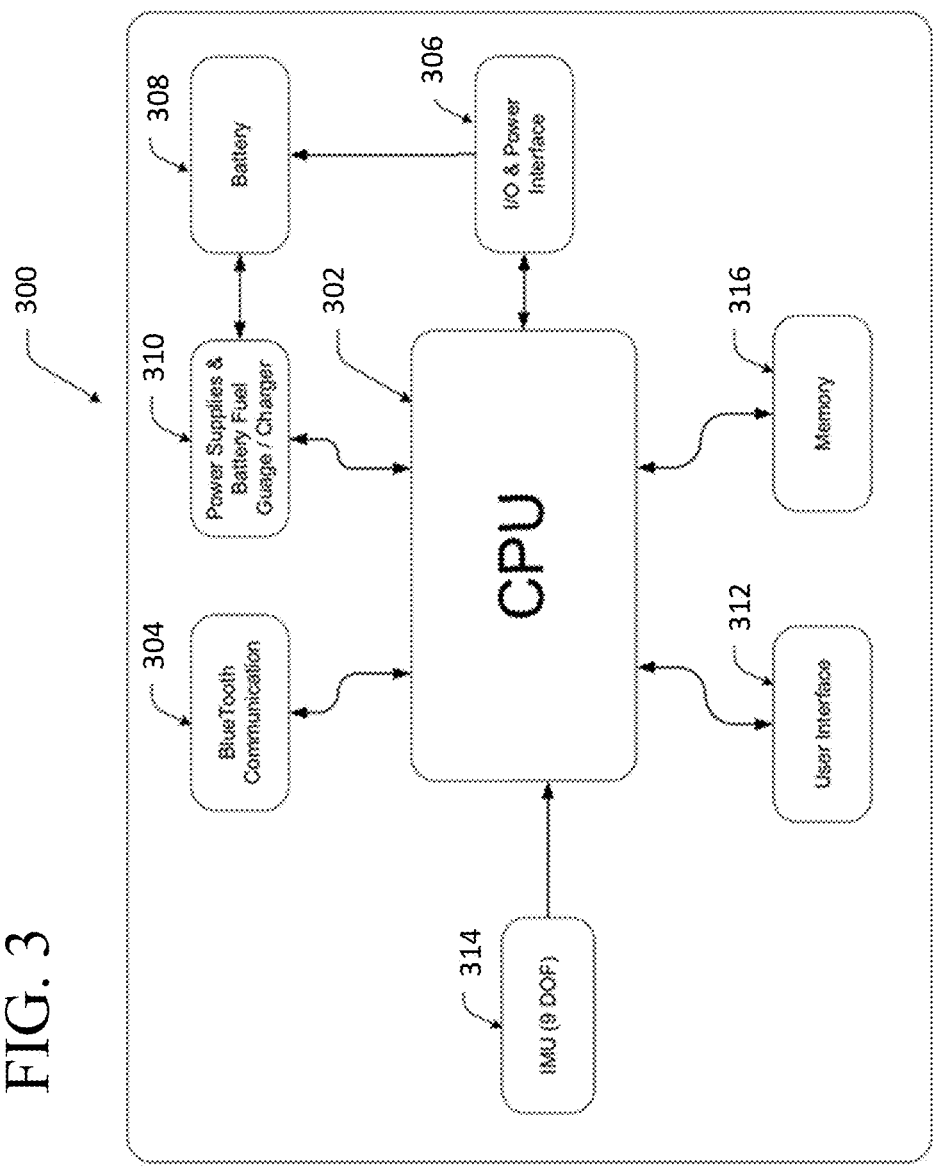
FIG. 3 is a block diagram of an example ultrasound remote controller.

FIG. 3 is a block diagram of an example ultrasound remote controller 300. The ultrasound remote controller 300, shown in FIG. 3, can function according to an applicable device for remotely controlling an ultrasound system, such as the ultrasound remote controller 210 shown in FIG. 2. Specifically, the ultrasound remote controller 300, shown in FIG. 3, can function according to an applicable device for remotely controlling a main processing console of an ultrasound system, such as the ultrasound remote controller 210 shown in FIG. 2.

The ultrasound remote controller 300 includes a central processing unit 302 (herein "CPU 302"). The CPU 302 can be used to perform the basic computational requirements of the peripherals either built into the CPU 302 or externally connected to the CPU 302. Specifically, the CPU 302 can perform the functionalities provided for by the ultrasound remote controller 300. For example, the CPU 302 can perform processing for transmitting operational instructions from the ultrasound remote control 300 for controlling a main processing console of an ultrasound system.

The CPU 302 can control or access one or more paths of communication external to the ultrasound remote controller 300. Specifically, the CPU 302 can cause the ultrasound remote controller 300 to transmit operational instructions over the communication paths external to the ultrasound remote controller 300 for remotely controlling an ultrasound system. Further, the CPU 302 can receive instructions for programming the ultrasound remote controller 300 over the communication paths external to the ultrasound remote controller 300, e.g. as part of remotely controlling an ultrasound system.

Communication paths accessed by the CPU 302 can be formed through a communication interface of the ultrasound remote controller 300. Specifically, a communication path can be a wireless communication path formed through a Bluetooth communication interface 304 formed as part of a communication interface of the ultrasound remote controller 300. More specifically, the Bluetooth communication interface 304 can provide a 2-way wireless communication link between an ultrasound system and the ultrasound remote controller 300. While the ultrasound remote controller 300 is shown to include a Bluetooth communication interface 304, in various embodiments, the ultrasound remote controller 300 can include a wireless communication interface configured to operate according to an applicable wireless protocol, such as a Wi-Fi protocol.

The ultrasound remote controller 300 can also include an I/O and power interface 306 that serves as another communication path for the ultrasound remote controller 300. This path can be realized with either a hard connection or inductively coupled, acoustic, or other non-wired manner. The I/O and power interface 306 can be used to receive power for the ultrasound remote controller 300. Specifically, the I/O and power interface 306 can receive power through either or both a wired or wireless manner at the ultrasound remote controller 300. Further the I/O and power interface 306 can receive data, e.g. programming instructions, through either or both a wired or wireless manner at the ultrasound remote controller 300. For example, the I/O and power interface 306 can receive data indicating associated of specific control functions with specific contexts of ultrasound procedures.

The I/O and power interface 306 can connect to a battery 308 included as part of the ultrasound remote controller 300 as well as the CPU 302. The connection to the battery 308 can allow power received at the I/O and power interface 306 to charge the battery 308. Further, the connection to the CPU 306 from the I/O and power interface 306 can be used to provide instructions to the CPU 306, e.g. software/firmware updates. Additionally, the connection to the CPU 306 from the I/O and power interface 306 can be used to interrogate the overall status of the ultrasound remote controller 300.

In the example ultrasound remote controller 300 shown in FIG. 3, the battery 308 is connected to a power supplies & battery fuel gage/charger 310. The power supplies & battery fuel gage/charger 310 can monitor the overall charge level of the battery 308. Further, the power supplies & battery fuel gage/charger 310 can control charging of the battery 308, e.g. through power received at the I/O and power interface 306. The power supplies & battery fuel gage/charger 310 can also provide necessary power supplies to other components of the ultrasound remote controller 300.

The example ultrasound remote controller 300 shown in FIG. 3 includes a user interface 312. The user interface 312 can function according to an applicable user interface controller, such as the user interface controllers described herein. Specifically, the user interface 312 can provide ultrasound control functions to an operator for remotely controlling an ultrasound system. Further, the user interface 312 can receive input for ultrasound control functions from an operator for purposes of remotely controlling an ultrasound system. The user interface 312 can communicate with the CPU 302 if there are any actions desired by an operator of the ultrasound remote controller 300. For example, the user interface 312 can provide input for one or more ultrasound control functions/operational instructions generated from the input for the one or more ultrasound control functions to the CPU 302. In receiving input for one or more ultrasound control functions, the user interface 312 can be constructed with simple push buttons or an active display and touch panel.

The example ultrasound remote controller 300 shown in FIG. 3 also includes an inertial motion unit (herein "IMU 314"). The IMU 314 can be configured to identify geometric data of the ultrasound remote controller 300. Specifically, the IMU can gather geometric data that includes one or a combination of motion, position, and orientation of the ultrasound remote controller 300. The IMU 314 can include applicable sensors for measuring one or a combination of motion, position, and orientation of the ultrasound remote controller 300. Specifically, the IMU 314 can include an applicable combination of corresponding sensors to gather geometric data for one to nine degrees of freedom at the ultrasound remote controller 300. For example, the IMU 314 can include three sensors to gather geometric data for three degrees of freedom at the ultrasound remote controller 300, six sensors to gather geometric data for six degrees of freedom at the ultrasound remote controller 300, or nine sensors to gather geometric data for nine degrees of freedom at the ultrasound remote controller 300.

Geometric data gathered by the IMU 314 can be transmitted by the Bluetooth communication 304, or an applicable communication interface, to a main processing console of an ultrasound system, e.g. as part of operational instructions. In turn, the main processing console can use the geometric data to process image data, gather image data, and present images as part of remotely controlling the main processing console through the ultrasound remote controller 300. For example, geometric information from the IMU 314 can be used by the ultrasound system to keep track of the relative position of the ultrasound remote controller 300. Further in the example, the geometric information can be used to display a position of the ultrasound remote controller 300 in a body marker image.

In various embodiments, geometric data of the ultrasound remote controller 300 can correspond to geometric data of an ultrasound transducer. In particular, when the ultrasound remote controller 300 is affixed to an ultrasound transducer, geometric data of the ultrasound remote controller 300 can correspond to geometric data of the ultrasound transducer, e.g. a position of the ultrasound transducer. For example, the ultrasound remote controller 300 can be affixed above an ultrasound transducer, and a position of the ultrasound remote controller 300 with respect to a patient can be a position of the ultrasound transducer with respect to the patient. In turn, the corresponding geometric data of the ultrasound transducer, as determined based on geometric data of the ultrasound remote controller 300, can be used to remotely control operation of a main processing console of an ultrasound using the ultrasound remote controller 300. Specifically, geometric data of an ultrasound transducer, e.g. a tracked position of the ultrasound transducer, can be sent to a main processing console of an ultrasound system, e.g. by a communication interface. Subsequently, the geometric data of the ultrasound transducer can be used to control operation of the main processing console.

The ultrasound remote controller 300, e.g. either or both the IMU 314 and the CPU 302, can identify geometric data of an ultrasound transducer based on geometric data of the ultrasound remote controller 300. Specifically, the ultrasound remote controller 300 can identify geometric data of an ultrasound transducer based on geometric data of the ultrasound remote controller 300 when the ultrasound remote controller 300 is affixed to the ultrasound transducer. For example, the ultrasound remote controller 300 can identify an ultrasound transducer is tilted at 45° when geometric data of the ultrasound remote controller 300 affixed to the ultrasound transducer indicates the ultrasound remote controller 300 is tilted at 45°.

Further, the ultrasound remote controller 300 can identify geometric data of an ultrasound transducer using geometric data of the ultrasound remote controller 300 based on design properties of the ultrasound transducer. Design properties of an ultrasound transducer can include a shape, a size, and other applicable design properties of the ultrasound transducer. For example, if an ultrasound transducer is two inches in height, then the ultrasound remote controller 300 can identify a position of the ultrasound transducer as two inches below a position of the ultrasound remote controller 300 affixed to the ultrasound transducer. As discussed previously, geometric data of an ultrasound transducer can be used to set a transducer location on a body marker image prior to saving the image.

The ultrasound remote controller 300 can identify design properties of an ultrasonic transducer, e.g. for purposes of identifying geometric data of the ultrasonic transducer, based on a received unique identifier of the transducer. For example, the ultrasound remote controller 300 can identify design properties of an ultrasonic transducer from a unique identifier indicating the type of transducer of the ultrasonic transducer. Subsequently, the ultrasound remote controller 300 can use the design properties to calibrate the ultrasound remote controller 300 with the ultrasound transducer for purposes of identifying geometric data of the ultrasound transducer.

A unique identifier of an ultrasound transducer can be received by the ultrasound remote controller 300 from an ultrasound transducer through an electrical connection formed by an electrical coupler between the ultrasound remote controller 300 and the ultrasound transducer. Specifically, a unique identifier of an ultrasound transducer can be transmitted to the ultrasound remote controller 300 through a selective grounding scheme at the ultrasound remote controller 300 where external input and output lines are pulled low to provide a known code of the unique identifier to the ultrasound remote controller, e.g. through an ultrasound transducer. The unique identifier can then be used to calibrate geometric data of the ultrasound remote controller 300 with respect to an ultrasound transducer in order to identify geometric data of the ultrasound remote controller 300.

The ultrasound remote controller 300 also includes a memory 316 for storing either or both program as well as runtime workspace items. The memory 316 can include both volatile and non-volatile memory. Data stored in the memory can include backgrounds for the user interface 312, drivers for peripherals, general program, use log and the like. It is understood that as integration of the ultrasound remote controller 300 improves over time to incorporate more of a system on chip manner that a number if not all of the external peripherals depicted FIG. 3 can be integrated directly into the CPU 302.

Figure 4:
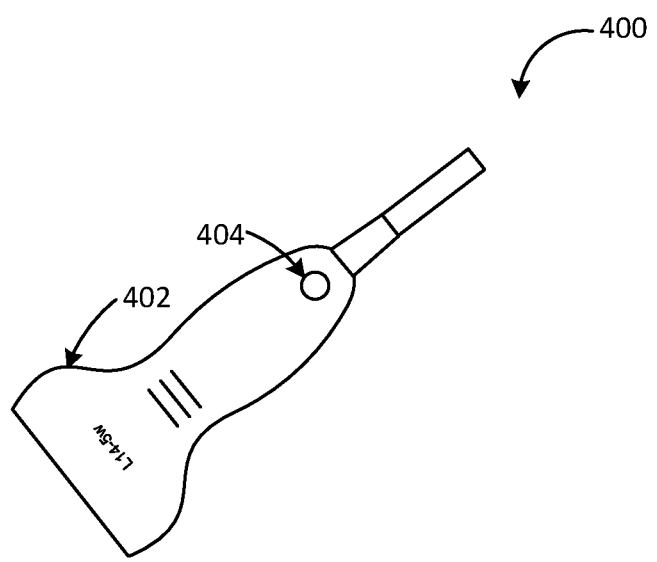
FIG. 4 illustrates a system for physically affixing an ultrasound remote controller to an ultrasound transducer.

FIG. 4 illustrates a system 400 for physically affixing an ultrasound remote controller to an ultrasound transducer 402. The system 400 can be used to affix an applicable ultrasound remote controller, such as the ultrasound remote controllers described herein, to the ultrasound transducer 402. In particular, the system 400 can be used to affix an ultrasound remote controller to the ultrasound transducer 402 for purposes of remotely controlling a main processing console of an ultrasound system including the ultrasound transducer 402.

The transducer 402 includes a physical coupler for physically affixing an ultrasound remote controller to the transducer 402. Specifically, the ultrasound transducer 402 has an adhesive orientation device/connection device 404 attached to the proximal area of the linear transducer 402. This connection device 404 is intended to not only just provide a place for an ultrasound remote controller to attach to the transducer 402 buts can also ensure consistent placement of the ultrasound remote controller. Additionally, the connection device 404 can support electrical connections/communications with an ultrasound remote controller. Further, the connection device 404 can be used to transmit an indication of a transducer type of the transducer 402. In turn, basic geometry and transducer design parameters can be automatically identified from the indication of the transducer type without the need for a user to perform a separate setup step, e.g. for purposes of calibrating an ultrasound remote controller with the transducer 402.

Figure 5:
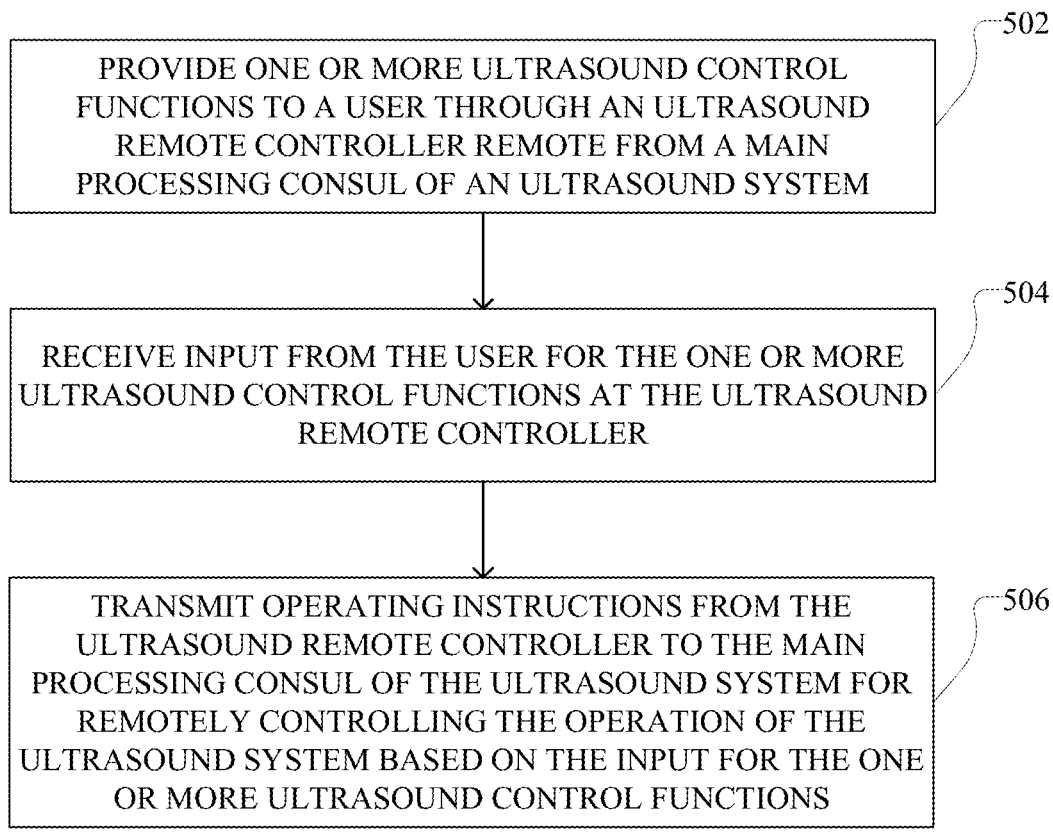
FIG. 5 is a flowchart of an example method of remotely controlling an ultrasound system through an ultrasound remote controller.

FIG. 5 is a flowchart 500 of an example method of remotely controlling an ultrasound system through an ultrasound remote controller. The example method shown in FIG. 5 can be performed by an applicable ultrasound remote controller, such as the example ultrasound remote controllers shown in FIGS. 2 and 3.

At step 502, one or more ultrasound control functions are provided to a user through an ultrasound remote controller that is remote from a main processing console of an ultrasound system. The one or more ultrasound control functions can be provided to a user through an applicable user interface, such as a user interface controller described with respect to FIG. 2 or the user interface 312 described with respect to FIG. 3. Further, the one or more ultrasound control functions can be provided to a user through the ultrasound remote controller when either the ultrasound remote controller is affixed to an ultrasound transducer of the ultrasound system or when the ultrasound remote controller is separate from the ultrasound transducer of the ultrasound system.

At step 504, input is received from the user at the ultrasound remote controller for the one or more ultrasound control functions provided to the user. Specifically, the input can be received from the user at the user interface/user interface controller. More specifically, the input can be received from the user based on the user's interactions with one or a combination of a touch-based display, a camera or sensor, physical buttons, and physical sliders at the user interface/user interface controller. For example, the input can be received based on the user's interactions with visual annotations of the ultrasound control functions presented to the user through a touch-based display.

At step 506, operational instructions are transmitted from the ultrasound remote controller to the main processing console of the ultrasound system for remotely controlling operation of ultrasound system based on the input for the one or more ultrasound control functions. Specifically, operational instructions can be generated by the user interface/user interface controller based on the received input and subsequently transmitted through a communication interface at the ultrasound remote controller to the main processing console of the ultrasound system. The operational instructions can be transmitted over a wireless connection from the ultrasound remote controller to the main processing console of the ultrasound system. Alternatively, the operational instructions can be transmitted over a wired connection, e.g. through an ultrasound transducer, from the ultrasound remote controller to the main processing console of the ultrasound system. Subsequently, the main processing console can operate according to the operational instructions as part of remotely controlling operation of the ultrasound system using the ultrasound remote controller.

FIG. 6 is a flowchart 600 of another example method of remotely controlling an ultrasound system through an ultrasound remote controller. The example method shown in FIG. 6 can be performed by an applicable ultrasound remote controller, such as the example ultrasound remote controllers shown in FIGS. 2 and 3.

At step 602, an ultrasound remote controller is physically secured to an ultrasound transducer of an ultrasound system to remotely control the ultrasound system. The ultrasound remote controller can be physically secured to an ultrasound transducer of the ultrasound system using an applicable coupling mechanism such as the physical couplers described herein. Further, in being physically secured to an ultrasound transducer of the ultrasound system, the ultrasound remote controller can be electrically coupled to the ultrasound transducer through one or more electrical connections. For example, the ultrasound remote controller can be electrically coupled to the ultrasound transducer through one or more electrical connections formed through a physical coupler used to affix the ultrasound remote control to the ultrasound transducer.

At step 604, geometric data of the ultrasound remote controller is identified at the ultrasound remote controller. An applicable mechanism for identifying geometric data of the ultrasound remote controller at the ultrasound remote controller, such as the IMU 314 can identify geometric data for the ultrasound remote controller. Geometric data of the ultrasound remote controller, can include one or a combination of a motion, a position, and an orientation of the ultrasound remote controller.

At step 606, the geometric data of the ultrasound remote controller is calibrated based on design properties of the ultrasound transducer to identify geometric data of the ultrasound transducer. Specifically, the ultrasound remote controller can identify one or a combination of a motion, a position, and an orientation of the ultrasound remote controller based on design properties of the ultrasound remote controller and geometric data of the ultrasound remote controller. The ultrasound remote controller can identify design properties of the ultrasound remote controller based on a unique identifier indicating a transducer type of the ultrasound transducer. Specifically, the ultrasound remote controller can store a list of design properties of various types of ultrasound transducers. Then, based on the transducer type of the ultrasound transducer, the ultrasound remote controller can query the list of design properties of the various ultrasound transducers to identify the design properties of the ultrasound transducer.

At step 608, operating instructions including the geometric data of the ultrasound transducer are transmitted to the main processing console for remotely controlling operation of the main processing console through the ultrasound remote controller. For example, the geometric data of the ultrasound transducer can be used to show a position of the ultrasound transducer in a body marker image. The operating instructions, including the geometric data, can be wirelessly transmitted to the main processing console from the ultrasound remote controller over a wireless communication channel. Further, the operations instructions, including the geometric data, can be transmitted to the main processing console from the ultrasound remote controller through the ultrasound transducer.

While the disclosure has been made only with reference to ultrasound systems, the systems and methods for remotely controlling ultrasound systems described herein can be used in conjunction with other applicable medical system. For example, the systems and methods described herein can be used for remote control of biopsy systems, laparoscopic tools, and ablation devices.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. An ultrasound remote controller for an ultrasound system including a main processing console and a plurality of ultrasound transducers, the ultrasound remote controller being attachable to, and detachable from, each of the plurality of ultrasound transducers to allow a user to remotely control the main processing console from a distance, the ultrasound remote controller comprising:
   a user interface controller configured to provide one or more ultrasound control functions and receive input for the one or more ultrasound control functions from the user;
   a communication interface configured to transmit operational instructions to the main processing console for remotely controlling operation of the main processing console through the ultrasound remote controller based on the input for the one or more ultrasound control functions received by the user interface controller; and
   an inertial motion unit to determine geometric data of the ultrasound remote controller, the geometric data of the ultrasound remote controller including one or more of a motion, a position, or an orientation of the ultrasound remote controller,
   wherein the ultrasound remote controller:
   identifies properties of a first ultrasound transducer including at least one of a shape, size, or type of the first ultrasound transducer via an identifier received from the first ultrasound transducer and calibrates the geometric data of the ultrasound remote controller to identify geometric data of the first ultrasound transducer, the geometric data of the first ultrasound transducer including one or more of a motion, a position, or an orientation of the first ultrasound transducer, and
   sends the geometric data of the first ultrasound transducer to the main processing console.

2. The ultrasound remote controller of claim 1, wherein the operational instructions are used to control operation of the main processing console as part of remotely controlling operation of the ultrasound system through the ultrasound remote controller.

3. The ultrasound remote controller of claim 1, wherein the operational instructions are used to control operation of the first ultrasound transducer as part of remotely controlling operation of the ultrasound system through the ultrasound remote controller.

4. The ultrasound remote controller of claim 1, wherein the one or more ultrasound control functions provided by the user interface controller are changed based on a context of a type of medical procedure performed by the user using the ultrasound system.

5. The ultrasound remote controller of claim 1, wherein the one or more ultrasound control functions include at least one of a freeze control, a change depth control, a gain control, a storage control, an auto-optimization control, a set reference control, a start clip control, a change mode control, a move region of interest control, a biopsy guide control, and a body marker select control.

6. The ultrasound remote controller of claim 1, further comprising a camera, wherein the user interface controller is configured to receive the input as a gesture via the camera.

7. The ultrasound remote controller of claim 1, wherein the user interface controller includes a user display for presenting visual annotations of the one or more ultrasound control functions to the user, and the input for the one or more ultrasound control functions is received from the user based on the user interpreting the visual annotations of the one or more ultrasound control functions.

8. The ultrasound remote controller of claim 1, wherein the user interface controller is configured to provide haptic feedback to the user based on user interaction with the user interface controller, and the input for the one or more ultrasound control functions is received from the user based on the user interpreting the haptic feedback.

9. The ultrasound remote controller of claim 1, wherein the communication interface is a wireless communication interface and the communication interface is further configured to transmit the operational instructions to the main processing console, at least in part, over a wireless connection.

10. The ultrasound remote controller of claim 1, wherein the ultrasound remote controller is configured to receive power over a wired connection.

11. The ultrasound remote controller of claim 1, wherein the ultrasound remote controller is configured to receive power over a wireless connection.

12. The ultrasound remote controller of claim 1, further comprising a physical coupler configured to physically affix the ultrasound remote controller to different types of ultrasound transducers, including the first ultrasound transducer, irrespective of varying properties of the different types of ultrasound transducers.

13. The ultrasound remote controller of claim 1, wherein the ultrasound remote controller includes an electronic coupler configured to electrically connect the ultrasound remote controller to the first ultrasound transducer through one or more electrical connections.

14. The ultrasound remote controller of claim 13, wherein the electronic coupler is configured to electrically connect the ultrasound remote controller to the first ultrasound transducer through the one or more electrical connections when the ultrasound remote controller is physically affixed to the first ultrasound transducer through a physical coupler.

15. The ultrasound remote controller of claim 13, wherein the communication interface is further configured to transmit the operational instructions to the main processing console through the one or more electrical connections and the first ultrasound transducer.

16. The ultrasound remote controller of claim 1, wherein the inertial motion unit includes one of three or six sensors to detect one or a combination of the motion, the position, and the orientation of the ultrasound remote controller.

17. The ultrasound remote controller of claim 1, further comprising a memory to store a list of properties associated with various types of ultrasound transducers, the properties including one or more of a size or shape of the various types of ultrasound transducers, and wherein the ultrasound remote controller is configured to query the list of properties to identify one or more properties of the first ultrasound transducer based on an identified type of first ultrasound transducer and use the list of properties to calibrate the geometric data of the ultrasound remote controller to identify the geometric data of the first ultrasound transducer.

18. The ultrasound remote controller of claim 1, wherein the user interface controller provides at least one control that has a first function when the user is performing a first type of medical procedure using the ultrasound system and a second function when the user is performing a second type of medical procedure using the ultrasound system.

19. The ultrasound remote controller of claim 1, wherein the geometric data of the first ultrasound transducer is used by the main processing console to automatically annotate an ultrasound image with a position of the first ultrasound transducer.

20. An ultrasound imaging system comprising:
a main processing console;
a plurality of ultrasound transducers; and
an ultrasound remote controller being attachable to, and detachable from, each of the plurality of ultrasound transducers to allow a user to remotely control the main processing console from a distance, the ultrasound remote controller comprising:
a user interface controller configured to provide one or more ultrasound control functions and receive input for the one or more ultrasound control functions from the user;
a communication interface configured to transmit operational instructions to the main processing console for remotely controlling operation of the main processing console through the ultrasound remote controller based on the input for the one or more ultrasound control functions received by the user interface controller; and
an inertial motion unit to determine geometric data of the ultrasound remote controller, the geometric data of the ultrasound remote controller including one or more of a motion, a position, or an orientation of the ultrasound remote controller,
wherein the ultrasound remote controller:
identifies properties of a first ultrasound transducer including at least one of a shape, size, or type of the first ultrasound transducer via an identifier received from the first ultrasound transducer and calibrates the geometric data of the ultrasound remote controller to identify geometric data of the first ultrasound transducer, the geometric data of the first ultrasound transducer including one or more of a motion, a position, or an orientation of the first ultrasound transducer, and
sends the geometric data of the first ultrasound transducer to the main processing console.

* * * * *